United States Patent [19]

Arndt et al.

[11] 4,177,054

[45] Dec. 4, 1979

[54] 1,2,3-THIADIAZOLE-5-CARBOXYLIC ACID DERIVATIVES, HERBICIDAL AND GROWTH REGULATING COMPOSITIONS CONTAINING THE SAME AND PROCESS FOR MAKING SAME

[75] Inventors: Friedrich Arndt; Hans-Rudolf Krüger; Reinhart Rusch, all of Berlin, Fed. Rep. of Germany

[73] Assignee: Schering Aktiengesellschaft, Berlin and Bergkamen, Fed. Rep. of Germany

[21] Appl. No.: 918,462

[22] Filed: Jun. 23, 1978

[30] Foreign Application Priority Data

Jun. 23, 1977 [DE] Fed. Rep. of Germany ....... 2728523

[51] Int. Cl.$^2$ ...................... C07D 285/06; A01N 9/12
[52] U.S. Cl. ........................................ 71/90; 546/209; 546/277; 544/134; 548/127
[58] Field of Search ....... 260/293.68, 302 D, 294.8 D; 544/134; 71/90

[56] References Cited

U.S. PATENT DOCUMENTS 3,940,407  2/1976  Muchowski et al. ........... 260/302 D

OTHER PUBLICATIONS

Pain et al., "J. Chem. Soc.", (1965), pp. 5166-5176.
Raap et al., "Can. J. Chem.", vol. 46, pp. 1057-1063, (1968).
Shafiee, "J. Het. Chem.", vol. 13, pp. 301-304, (1976).
Shafiee et al., "J. Het. Chem.", vol. 14, pp. 567-571, (1977).
Noller, "Chemistry of Organic Compounds", 2nd Edition, p. 161, (1957).

*Primary Examiner*—Alan L. Rotman
*Assistant Examiner*—Robert T. Bond

*Attorney, Agent, or Firm*—Michael J. Striker

[57] ABSTRACT

1,2,3-thiadiazole-5-carboxylic acid derivatives having herbicidal and growth regulating activity and having the formula

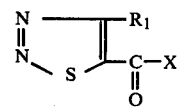

I in which $R_1$ is hydrogen or is alkyl of which the chain may be interrupted in one or several places by oxygen or sulfur or which may be substituted by halogen and in which X is (a) —Y—$R_2$, wherein $R_2$ is hydrogen, alkyl which may be substituted, aryl which may also be substituted, aryl-$C_1$-$C_2$-alkyl which may also be substituted, or a univalent metal equivalent and wherein Y is oxygen or sulfur, or (b) wherein X constitutes the residue

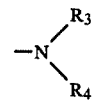

wherein $R_3$ and $R_4$ may be the same or different and have the meaning further defined in claim 1 of the accompanying specification.

The compounds are soil- or leaf-applicable herbicides with a high activity against seed weeds and resistant weeds.

66 Claims, No Drawings

1,2,3-THIADIAZOLE-5-CARBOXYLIC ACID DERIVATIVES, HERBICIDAL AND GROWTH REGULATING COMPOSITIONS CONTAINING THE SAME AND PROCESS FOR MAKING SAME

BACKGROUND OF THE INVENTION

The invention relates to 1,2,3-thiadiazole-5-carboxylic acid derivatives having a herbicidal and growth regulating activity and compositions containing the same.

Weed suppression in agricultural production has three essential functions: it must insure the growth of the crops it must assure the usefulness of the products harvested, and it must improve the working and production conditions. Effective weed suppression frequently constitutes the condition precedent to complete mechanization of a line of operation such as for instance grain, maize or beet planting, or form the basis for introducing new agricultural working methods and seeding processes, as for instance the direct speed process in case of maize, grain, soybean and cotton.

The prior art herbicides do not meet to the optimum degree the functions described, which functions have the highest significance for the progress of the agricultural and horticultural industry. There is therefore a substantial need for improving the technique of combating weeds.

An object of the present invention is therefore the provision of an agent which permits an improvement of the weed suppression techniques.

SUMMARY OF THE INVENTION

This problem is met by an agent which contains at least one compound of the formula

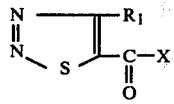     I in which $R_1$ is hydrogen or is alkyl of which the chain may be interrupted in one or several places by oxygen or sulfur and which may be substituted by halogen and in which X constitutes (a) the residue $-Y-R_2$ in which $R_2$ is hydrogen, alkyl, which may be substituted, aryl, which may also be substituted, aryl-$C_1$-$C_2$-alkyl which may also be substituted, or constitutes a univalent metal equivalent and wherein Y is oxygen or sulfur, or wherein X constitutes (b) the residue

in which $R_3$ and $R_4$ are the same or different and may be hydrogen, $C_1$-$C_{18}$ alkyl which may also be substituted, $C_2$-$C_8$-alkenyl or alkinyl, aryl-$C_1$-$C_3$-alkyl which may also be substituted, a $C_3$-$C_8$-cycloaliphatic hydrocarbon residue which may also be substituted, $C_3$-$C_8$-cycloalkyl-$C_1$-$C_3$-alkyl- which may also be substituted, an aromatic hydrocarbon residue which may be substituted in one or several places by $C_1$-$C_6$-alkyl and/or halogen and/or $C_1$-$C_6$-alkoxy and/or nitro and/or trifluoromethyl or wherein $R_3$ and $R_4$ together with the adjoining nitrogen atom constitute a morpholino- piperidino- or pyrrolidino group.

The compounds of the invention are characterized by a soil- and/or leaf-herbicidal activity against seed weeds and resistant weeds. Their activity is partly systemic. They are particularly effective against dicotyl and monocotyl weed types of the families Digitalis, Trifolium, Portulaca, Papaver, Daucus, Kochia, Gypsophyla, Lactuca, Solanum, Escholtzia, Cheiranthus, Phacelia, Euphorbia, Linum, Convolvulus, Brassica, Datura, Cichorium, Ipomoea, Setaria, Agrostis, Phleum, Alopecurus, Phalaris, Dactylis, Festuca, Arrhenaterum, Lolium, Bromus, Avena, Allium, Cucumis, Medicago, Stellaria, Senecio, Matricaria, Lamium, Centaurea, Amaranthus, Galium, Chrysanthemum, Polygonum, Sorghum, Alopecurus, Echinochloa, Digitaria, Cyperus, Poa and others. The amounts employed are about 0.5 to 5 kg of active agent per about 2.5 acres.

A selective application is possible for instance in grain, cotton, soybean and plantation cultures. The highest activities are displayed by these agents, if they are sprayed onto a preexisting weed growth or are sprayed prior to the emergence. The so-called seed cultures can also be drilled a few days after spraying.

The individual compounds of the present invention may also modify the natural development of the plants so as to obtain various properties which may be agriculturally or horticulturally valuable.

The application of the compounds of the invention can be effected onto seeds or seedlings prior to or after emergence, onto roots, stems, leaves, blossoms, fruits or other plant parts.

The modification of the natural growth normally can be ascertained visually by changes of growth, of shape, of color or of structure of the treated plant or any of its parts.

The visually perceptible morphological modifications always presuppose a change of physiological and biochemical processes in the plant. The art has numerous analytical procedures to determine the kind and degree of such biochemical and physiological changes. Among these there may be mentioned the following changes of development of the plants as may be caused by the compounds of the invention:

Inhibition of the vertical growth

Inhibition of the root development

Stimulation of the budding and shoots

Intensifying of the formation of plant pigments

Defoliation.

The compounds of the invention, surprisingly, meet all functions necessary for an improvement of the weed suppression technique to an extent heretofore unknown.

Among the compounds of the invention the described effects are particularly obtained by those in which in the above formula I $R_1$ is hydrogen or $C_1$-$C_4$-alkyl which may be substituted by chlorine or bromine, for instance methyl, propyl, chloromethyl or bromomethyl, $R_2$ is hydrogen or $C_1$-$C_4$-alkyl, for instance methyl, ethyl, propyl, isopropyl, butyl, or is an aromatic hydrocarbon such as phenyl, 4-chlorophenyl, 4-nitrophenyl, 3-chlorophenyl, 2-chlorophenyl or 4-methylphenyl, or is an alkali metal atom, preferably lithium, sodium or potassium, or is a corresponding equivalent of a bivalent metal, for instance zinc, manganese, calcium, magnesium or barium, and wherein Y is oxygen or sulfur and wherein if X is constituted by the residue

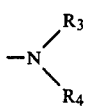

$R_3$ and $R_4$ are the same or different and may be hydrogen, $C_1$–$C_8$ alkyl which may be substituted by halogen, phenoxy, dialkylamino, alkoxy, alkoxycarbonyl, $C_2$–$C_6$ alkenyl or alkinyl, $C_3$–$C_8$-cycloalkylmethyl which may also be substituted, $C_6$–$C_8$ cycloalkyl which may also be substituted, or wherein $R_3$ and $R_4$ may be phenyl, chlorophenyl, nitrophenyl or methylphenyl.

More specifically, the residues identified as $R_3$ and $R_4$ may for instance be hydrogen, or in case of $C_1$–$C_{18}$ alkyl may be methyl, ethyl, propyl, isopropyl, n-butyl, tert-butyl, 2,2-dimethyl-1-propyl, n-heptyl, n-nonyl, n-undecyl, n-octadecyl, 3-methylbutyl, 4-methyl-2-pentyl, isobutyl, 3,3-dimethylbutyl, 2-butyl or 3,3-dimethyl-2-butyl, or in case of $C_1$–$C_{18}$, alkyl may be 2-chloroethyl, 3-chloropropyl, 3-bromopropyl, 2-bromoethyl, 1-phenoxy-2-propyl, 3-dimethylaminopropyl, 2-dimethylaminoethyl, 3-diethylaminopropyl, tetrahydrofurfuryl, ethoxycarbonylmethyl, cyanomethyl, 2,2-methoxyethyl or 2-ethoxyethyl, or in case of $C_3$–$C_8$ cycloalkyl-$C_1$-$C_3$-alkyl may be cyclohexylmethyl, 4-cyanocyclohexylmethyl, 4-hydroxymethylcyclohexylmethyl, 4-carbonylcyclohexylmethyl, cycloheptylmethyl or cyclooctylmethyl or cyclopropylmethyl, or in case of $C_2$–$C_8$-alkenyl or alkinyl may be 2-propenyl, 2-butenyl, 2-methyl-2-propenyl, 2-propinyl or 3-ethyl-1-pentine-3-yl, or in case of aryl-$C_1$–$C_3$-alkyl may be benzyl, 4-chlorobenzyl, 3-chlorobenzyl, 2-chlorobenzyl, 4-fluorobenzyl, 3-fluorobenzyl, 2-fluorobenzyl, 4-methylbenzyl, 3-methylbenzyl, 2-methylbenzyl, 3,4-methylenedioxybenzyl, 2,4-dichlorobenzyl, 3,4-dichlorobenzyl, 4-methoxybenzyl, 3-methoxybenzyl, 2-methoxybenzyl, 2-pyridylmethyl, 3-pyridylmethyl, 4-pyridylmethyl, α,α-dimethylbenzyl, 1-phenylethyl, 2-phenylethyl, 1,2-diphenylethyl, 2,2-diphenylethyl, 4-fluoro-α-methylbenzyl, 3-phenylpropyl or 2-furfuryl, or in case of a $C_3$–$C_8$-cycloaliphatic hydrocarbon residue may be cyclopropyl, cyclopentyl, cyclohexyl, 2-methylcyclohexyl, 3-methylcyclohexyl, 4-methylcyclohexyl, 1-ethinylcyclohexyl, cycloheptyl or cyclooctyl, or in case of an aromatic hydrocarbon residue may be phenyl, 3-chlorophenyl, 2-chlorophenyl, 4-chlorophenyl, 2,4-dichlorophenyl, 4-fluorophenyl, 2-methylphenyl, 3-methylphenyl, 4-methylphenyl, 1-naphthyl, 2-methoxyphenyl, 3-methoxyphenyl or 4-nitrophenyl.

The compounds of the invention can be used either individually, or in mixture with each other or in mixture with other agents.

Depending on the particular purpose of use there may for instance be added to the compounds of the invention the following herbicidal agents:
substituted anilines,
substituted aryloxycarboxylic acids and their salts, esters and amides,
substituted ethers,
substituted arsonic acids and their salts, esters and amides,
substituted benzimidazoles
substituted benzisothiazoles,
substituted benzthiadiazinone dioxides,
substituted benzoxazines,
substituted benzoxazinones,
substituted benzthiazoles,
substituted benzothiadiazines,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates
substituted quinazolines,
substituted cycloalkylamidocarbonylthiol acids and their salts, esters and amides,
substituted cycloalkylcarbonylamido-thiazoles,
substituted dicarboxylic acids and their salts, esters and amides,
substituted dihydrobenzofuranylsulfonates,
substituted disulfides,
substituted dipyridylium salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinons,
substituted oxadiazolidinedione,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, esters and amides,
substituted piperidines,
substituted pyrazoles,
substituted pyrazolalkylcarboxylic acids and their salts, esters, and amides,
substituted pyrazolium salts,
substituted pyrazoliumalkylsulfates,
substituted pyridazines,
substituted pyridazones,
substituted pyridine-carboxylic acids and their salts, esters and amides,
substituted pyridines,
substituted pyridinecarboxylates,
substituted pyridinone,
substituted pyrimidone,
substituted pyrrolidine-carboxylic acids and their salts, esters and amides,
substituted pyrrolidines,
substituted pyrrolidones, substituted arylsulfonic acids and their salts, esters and amides,
substituted styrenes,
substituted tetrahydro-oxadiazinediones,
substituted tetrahydromethanoindenes,
substituted tetrahydro-diazol-thiones,
substituted tetrahydro-thiadiazine-thiones,
substituted tetrahydro-thiadiazolediones,
substituted aromatic thiocarboxylic acid amides,
substituted thiocarboxylic acids and their salts, esters and amides,
substituted thiolcarbamates,
substituted thiourea derivatives,
substituted thiophosphoric acids and their salts, esters and amides,
substituted triazines,
substituted triazoles
substituted uracils, and
substituted urethidindiones,
auxin,
α-(2-chlorophenoxy)-propionic acid,
4-chlorophenoxyacetic acid
2,4-dichlorophenoxyacetic acid,
indolyl-3-acetic acid,
indolyl-3-butyric acid,
α-naphthyl acetic acid,
β-naphthoxy acetic acid,
naphthylacetamide,
n-m-tolylphthalamido acid,
gibberellins,
S,S,S-tri-n-butyl-triethiophosphoric acid ester,
cytoquinines,
2-chloroethylphosphoric acid,
2-chloro-9-hydroxyfluorene-9-carboxylic acid,
2-chloroethyl-trimethylammoniumchloride,
N,N-dimethylaminosuccinic acid amide,
2-isopropyl-4-trimethylammonio-5-methylphenyl-piperidine-1-carboxylic acid esterchloride,
phenyl-isopropylcarbamate,
3-chlorophenyl-isopropylcarbamate,
ethyl-2-(3-chlorophenylcarbamoyloxy)-propionate,
maleic acid hydrazide,
2,3-dichloroisobutyric acid,
di-(methoxythiocarbonyl)disulfide,
1,1'-dimethyl-4,4'-bipyridylium-dichloride,
3,6-endoxohexahydrophthalic acid,
3-amino-1,2,4-triazole,
1,2,3-thiadiazolyl-5-yl-urea derivative,
1-(2-pyridyl)-3-(1,2,3-thiadiazole-5-yl)-urea
2-butylthio-benzthiazole,
2-(2-methylpropylthio)-benzthiazole,
3,4-dichloroisothiazole-5-carboxylic acid,
2,3-dihydro-5,6-dimethyl-1,4-dithiino-1,1,4,4-tetroxide,
arsenic acid,
cacodylic acid,
chlorates, preferably calcium chlorate, potassium chlorate, magnesium chlorate or sodium chlorate,
calcium cyanamide,
potassium iodide,
magnesium chloride,
abscisinic acid, nonanol,
N-(phosphonomethyl)-glycine-monoisopropyl-amine salt, and
N,N-bis-(phosphonomethyl)-glycine.

In addition there can also be used other additives for instance non-phytotoxic additives which in herbicides result in a synergistic increase of the activity and furthermore they can be used as wetting agents, emulsifiers, solvents and oily additives. The compounds of the invention or their mixture are preferably used in the form of compositions such as powders, dusting agents, granulates, solutions, emulsions or suspensions. There are added liquid and/or solid carrier materials or diluents and, if desired, wetting agents, adhesion promotion agents, emulsifiers and/or dispersing agents.

Suitable liquid carrier materials are, for instance, water, aliphatic and aromatic hydrocarbons, cyclohexanone, isophorone, dimethylsulfoxide, dimethylformamide, and furthermore mineral oil fractions.

As solid carrier materials there can be used mineral earths, for instance, tonsil, silicagel, talc, kaolin, attaclay, limestone, silicic acid, and plant products, for instance, flours.

There may also be added surface active agents, for instance calciumlignosulfonate, polyoxyethylene-alkylphenylether, naphthalenesulfonic acids and their salts, phenolsulfonic acid and their salts, formaldehyde condensation products, fatty alcohol sulfates, as well as substituted benzosulfonic acids and their salts.

The proportion of the active agent or agents can be varied in the different compositions within a broad range. The compositions may, for instance, contain about 10 to 80% by weight of active agents, 90 to 20% by weight of liquid or solid carrier materials and, if desired, up to 20% by weight of surface active agents in which case a corresponding reduction of the carrier materials is effected.

The application of the compounds of the invention and of the composition can be effected in conventional form, for instance with water as carrier materials in spray amounts of about 100 to 1000 liters to about 2.5 acres. The application of the agents is possible in the so-called "low-volume" and "ultra-low-volume" process as well as in the form of so-called microgranulates.

The new herbicides and growth regulating agents can be made in different ways.

(A) Compounds of the Formula

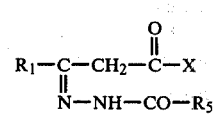

II may be reacted with thionylchloride, or (B) 1,2,3-thiadiazole-5-carboxylic acid halides of the formula

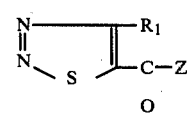

III may be reacted with compounds of the formula

H—X  IV in the presence of acid acceptors, or in the following specific case (C) 1,2,3-thiadiazole-5-carboxylic acid esters of the formula:

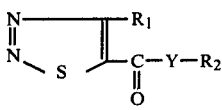

are reacted with amines of the formula

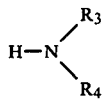

In the above formulae $R_1$, $R_2$, $R_3$, $R_4$, X and Y have the same meaning as in the above formula I, Z is halogen, preferably chlorine, and $R_5$ is $C_1$-$C_4$-alkoxy.

The reaction in all of these cases is carried out at a temperature between about 0° and 120° C. Preferred is a temperature between room temperature and the reflux temperature of the particular reaction mixture.

In order to effect the synthesis of the compounds of the invention the components are preferably used in about equimolar amounts. Suitable reaction media are solvents which are inert towards the reaction components. As such solvents there may be mentioned the following: halogenated hydrocarbons such as methylene chloride, chloroform and carbontetrachloride; aliphatic and aromatic hydrocarbons such as petrol ether, cyclohexane, benzene, toluene and xylene; alcohols, like methanol and ethanol; ketones, like acetone, methylisobutylketone and isophorone; ethers, like diethylether, tetrahydrofuran and dioxane, and carboxylic acid nitriles, like acetonitrile.

As acid acceptors there may be used organic bases such as triethylamine, N,N-dimethylaniline and pyridine bases, or inorganic bases, like oxides, hydroxides, and carbonates of the alkaline earth and alkali metals. Liquid bases, like pyridine can also serve simultaneously as solvents.

The compounds of the invention which are made by the above processes can be isolated in conventional form, for instance by distilling off the solvent at atmospheric or reduced pressure, by precipitation with water or by fractional distillation.

The following examples will further illustrate the making of the compounds of the invention.

EXAMPLE 1

4-Methyl-1,2,3-thiadiazole-5-carboxylic acid ethylester (Compound No. 1) of the formula

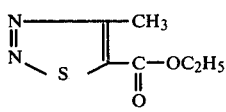

432.5 g (2 mol) of 3-ethoxycarbonylhydrazonoacetic acid ethylester of a melting point between 59° and 61° C. were added batchwise to 700 ml thionylchloride at 20° C. while stirring the mixture and cooling it by ice. The solution was then permitted to stand for 20 hours at room temperature. The excess thionylchloride was then distilled off and the remaining residue was subjected to fractional distillation under reduced pressure. There were thus obtained 284.9 g (83% of the calculated value) of 4-methyl-1,2,3-thiadiazole-5-carboxylic acid ethylester as a colorless liquid having a boiling point of 66° to 69° C./0.5 torr.

EXAMPLE 2

4-methyl-1,2,3-thiadiazole-5-carboxylic acid (Compound No. 2) of the formula

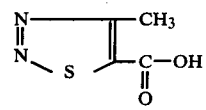

33.4 g (0.194 mol) of 4-methyl-1,2,3-thiadiazole-5-carboxylic acid ethylester were reacted with 80 ml of a 3 n methanol solution of sodium hydroxide and were permitted to stand for 16 hours at room temperature. The methanol was then withdrawn in a vacuum and the remaining sodium salt was washed with ether. The salt was subsequently dissolved in 200 ml water and acidified with dilute hydrochloric acid. It was then filtered off and subsequently washed with pentane.

Recyrstallization was effected from acetic acid ester/hexane.

The yield was 25.9 g=96% of the calculated value.

There were obtained colorless crystals of a melting point of 174° to 175° C.

EXAMPLE 3

4-methyl-1,2,3-thiadiazole-5-carboxylic acid-(4-fluorobenzylamide)

(Compound No. 3) of the formula

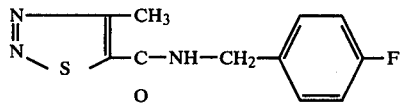

9.4 g (0.075 mol) of 4-fluorobenzylamine, dissolved in 100 ml of tetrahydrofuran were reacted at room temperature with 10.4 ml (0.075 mol) of triethylamine. A solution of 12.2 g (0.075 mol) of 4-methyl-1,2,3-thiadiazole-5-carboxylic acid chloride (b.p. 48° to 50° C./0.5 torr) dissolved in 50 ml tetrahydrofuran was then added dropwise at 10° C. upon stirring and cooling. Stirring was continued for 4 hours. After removing the precipitate by suction the filtrate was concentrated by evaporation and digested with ether.

Recrystallization was effected from ethanol.

The yield was 14.2 g=75.5% of the calculated value.

There were obtained colorless crystals of an m.p. of 106° to 107° C.

EXAMPLE 4

4-methyl-1,2,3-thiadiazole-5-carboxylic acid-(cyclohexylmethyl)-amide (Compound No. 4) of the formula

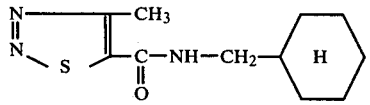

17.2 g (0.1 mol) of 4-methyl-1,2,3-thiadiazole-5-carboxylic acid ethylester dissolved in 30 ml of absolute ethanol were reacted at room temperature with 11.3 g (0.1 mol) of aminomethylcyclohexane and subsequently heated under reflux for 3 hours. The solution was thereafter concentrated by evaporation and the remaining oil was digested with isopropylether.

Recrystallization was effected from cyclohexane.

The yield was 22.9 g=96% of the calculated value.

There were obtained colorless crystals, m.p. 79° to 80° C.

Making of the starting product for Compound No. 3

EXAMPLE 3

The starting compound of this product is 4-methyl-1,2,3-thiadiazole-5-carboxylic acid chloride. In order to obtain this compound 103.6 g (0.72 mol) were added batchwise to 280 ml of thionylchloride. The mixture was then heated for 3½ hours under reflux. The excess thionylchloride was distilled off and the remaining residue was subjected to fractional distillation at a reduced pressure. There were obtained 102 g (87.2% of the calculated value) of the above starting compound for Example 3 in the form of a colorless liquid; b.p. 48° to 50° C./0.5 torr.

In an analogous manner there were obtained the following compounds of the invention.

| Compound No. | Name of Compound | Physical Constants |
|---|---|---|
| 5 | 4-methyl-1,2,3-thiadiazole-5-carboxylic acid-anilide | m.p.: 116°–117° C. |
| 6 | 4-methyl-1,2,3-thiadiazole-5-carboxylic acid-(2-chloro-anilide) | m.p.: 106°–107° C. |
| 7 | 4-methyl-1,2,3-thiadiazole-5-carboxylic acid-(3-chloro-anilide) | m.p.: 137°–138° C. |
| 8 | 4-methyl-1,2,3-thiadiazole-5-carboxylic acid-(3,4-dichloro-anilide) | m.p.: 135°–136° C. |
| 9 | 4-methyl-1,2,3-thiadiazole-5-carboxylic acid(4-chloro-2-methylanilide) | m.p.: 142°–143° C. |
| 10 | 4-methyl-1,2,3-thiadiazole-5-carboxylic acid-(2-methyl-anilide) | m.p.: 115°–116° C. |
| 11 | 4-methyl-1,2,3-thiadiazole-5-carboxylic acid-(3-methyl-anilide) | m.p.: 116°–117° C. |
| 12 | 4-methyl-1,2,3-thiadiazole-5-carboxylic acid-(4-methyl-anilide) | m.p.: 118°–119° C. |
| 13 | 4-methyl-1,2,3-thiadiazole-5-carboxylic acid-(3-trifluoro-methylanilide) | m.p.: 123°–124° C. |
| 14 | 4-methyl-1,2,3-thiadiazole-5-carboxylic acid-(4-fluoro-anilide) | m.p.: 108°–109° C. |
| 15 | 4-methyl-1,2,3-thiadiazole-5-carboxylic acid-(4-nitro-anilide) | m.p.: 179°–180° C. |
| 16 | 4-methyl-1,2,3-thiadiazole-5-carboxylic acid-(N-methyl-anilide) | m.p.: 84°–85° C. |
| 17 | 4-methyl-1,2,3-thiadiazole-5-carboxylic acid dimethyl-amide | m.p.: 120°–125° C. |
| 18 | 4-methyl-1,2,3-thiadiazole-5-carboxylic acid-(N-benzyl-N-2-propinylamide) | $n_D^{20}$: 1,5848 |
| 19 | 4-methyl-1,2,3-thiadiazole-5-carboxylic acid-(4-chloro-anilide) | m.p.: 121°–122° C. |
| 20 | 4-methyl-1,2,3-thiadiazole-5-carboxylic acid-(3,5-di-chloroanilide) | m.p.: 195°–196° C. |
| 21 | 4-methyl-1,2,3-thiadiazole-5-carboxylic acid benzylamide | m.p.: 63°–64° C. |
| 22 | 1,2,3-thiadiazole-5-carboxylic acid ethylester | b.p.: 55°–57° C. |
| 23 | 4-methyl-1,2,3-thiadiazole-5-carboxylic acid-(4-chloro-benzylamide) | m.p.: 109°–110° C. |
| 24 | 4-methyl-1,2,3-thiadiazole-5-carboxylic acid-(2-chloro-6-methylanilide) | m.p.: 133°–134° C. |
| 25 | 4-methyl-1,2,3-thiadiazole-5-carboxylic acid-(N-cyano-methyl-2,6-dimethylanilide) | m.p.: 118°–119° C. |
| 26 | 4-methyl-1,2,3-thiadiazole-5-carboxylic acid-(2,6-dimethyl-anilide) | m.p.: 100°–101° C. |
| 27 | 4-methyl-1,2,3-thiadiazole-5-carboxylic acid-(2,6-dichloro-anilide) | m.p.: 116°–118° C. |
| 28 | 4-methyl-1,2,3-thiadiazole-5-carboxylic acid diethyl-amide | m.p. 111°–114° C. |
| 29 | 4-methyl-1,2,3-thiadiazole-5-carboxylic acid-(2-pyridyl-methylamide) | m.p.: 75°–76° C. |
| 30 | 4-methyl-1,2,3-thiadiazole-5-carboxylic acid-(3-pyridyl-methylamide) | m.p.: 95°–96° C. |
| 31 | 4-methyl-1,2,3-thiadiazole-5-carboxylic acid-(2-chloro-benzylamide) | m.p.: 68° C. |
| 32 | 4-methyl-1,2,3-thiadiazole-5-carboxylic acid-(3,4-methylene-dioxybenzylamide) | m.p.: 87°–88° C. |
| 33 | 4-methyl-1,2,3-thiadiazole-5-carboxylic acid diisopropyl-amide | m.p.: 89°–91° C. |
| 34 | 4-methyl-1,2,3-thiadiazole-5-carboxylic acid-(N-benzyl-N-methylamide) | $n_D^{20}$ 1,5838 |
| 35 | 4-methyl-1,2,3-thiadiazole-5-carboxylic acid-(2,4-dichloro-benzylamide) | m.p.: 109°–111° C. |
| 36 | 4-methyl-1,2,3-thiadiazole-5-carboxylic acid-(3,4-dichloro-benzylamide) | m.p.: 109°–110° C. |
| 37 | 4-methyl-1,2,3-thiadiazole-5-carboxylic acid-(3-chloro-benzylamide) | m.p.: 64°–65° C. |
| 38 | 4-methyl-1,2,3-thiadiazole-5-carboxylic acid-(2-methoxy-benzylamide) | m.p.: 96°–97° C. |
| 39 | 4-methyl-1,2,3-thiadiazole-5-carboxylic acid-(3-methoxy-benzylamide) | m.p.: 73°–75° C. |
| 40 | 4-methyl-1,2,3-thiadiazole-5-carboxylic acid-(4-methoxy-benzylamide) | m.p.: 115°–117° C. |
| 41 | 4-methyl-1,2,3-thiadiazole-5-carboxylic acid-(4-methyl-benzylamide) | m.p.: 115°–116° C. |
| 42 | 4-methyl-1,2,3-thiadiazole-5-carboxylic acid-(2-fluorobenzyl-amide) | m.p.: 108°–109° C. |
| 43 | 4-methyl-1,2,3-thiadiazole-5-carboxylic acid-(N-ethyl-N-benzylamide) | $n_D^{20}$: 1,5751 |
| 44 | 4-methyl-1,2,3-thiadiazole-5-carboxylic acid-(N-benzyl-N-isopropylamide) | $n_D^{20}$: 1,5695 |
| 45 | 4-methyl-1,2,3-thiadiazole-5-carboxylic acid-(N-benzyl-N-butylamide) | $n_D^{20}$: 1,5623 |
| 46 | 4-methyl-1,2,3-thiadiazole-5-carboxylic acid-(3-methyl-benzylamide) | m.p.: 52°–53° C. |
| 47 | 4-methyl-1,2,3-thiadiazole-5-carboxylic acid-(2-naphthyl-methylamide) | m.p.: 108°–109° C. |
| 48 | 4-methyl-1,2,3-thiadiazole- | |

-continued

| Compound No. | Name of Compound | Physical Constants |
|---|---|---|
|  | 5-carboxylic acid-(3,5-dimethyl-benzylamide) | m.p.: 95°–96° C. |
| 49 | 4-methyl-1,2,3-thiadiazole-5-carboxylic acid-(4-tert-butylbenzylamide) | m.p.: 65°–68° C. |
| 50 | 4-methyl-1,2,3-thiadiazole-5-carboxylic acid cyclohexylamide | m.p.: 101°–102° C. |
| 51 | 4-methyl-1,2,3-thiadiazole 5-carboxylic acid cycloctylamide | m.p.: 110°–111° C. |
| 52 | 4-methyl-1,2,3-thiadiazole-5-carboxylic acid cycloheptylamide | m.p.: 110°–112 C. |
| 53 | 4-methyl-1,2,3-thiadiazole 5-carboxylic acid cyclopentylamide | m.p.: 87°–89° C. |
| 54 | 4-methyl-1,2,3-thiadiazole-5-carboxylic acid cyclopropylamide | m.p.: 89°–91° C. |
| 55 | 4-methyl-1,2,3-thiadiazole-5-carboxylic acid butylamide | $n_D^{20}$ : 1,5302 |
| 56 | 4-methyl-1,2,3-thiadiazole-5-carboxylic acid-(2-methyl-propylamide) | $n_D^{20}$ : 1,5267 |
| 57 | 4-methyl-1,2,3-thiadiazole-5-carboxylic acid-(1,1-dimethyl-ethylamide) | m.p.: 88°–90° C. |
| 58 | 4-methyl-1,2,3-thiadiazole-5-carboxylic acid-(2-propenyl-amide) | m.p.: 58°–59° C. |
| 59 | 4-methyl-1,2,3-thiadiazole-5-carboxylic acid-(ethoxy-carbonylmethylamide | $n_D^{20}$ : 1,5298 |
| 60 | 4-methyl-1,2,3-thiadiazole-5-carboxylic acid-(2-ethoxy-ethylamide) | $n_D^{20}$ : 1,5258 |
| 61 | 4-methyl-1,2,3-thiadiazole-5-carboxylic acid-(1,1-diethyl-2-propinylamide) | m.p.: 74°–75° C. |
| 62 | 4-methyl-1,2,3-thiadiazole-5-carboxylic acid-(2,2-diethoxy-ethylamide) | $n_D^{20}$ : 1,5089 |
| 63 | 4-methyl-1,2,3-thiadiazole-5-carboxylic acid-(3-dimethyl-aminopropylamide) | $n_D^{20}$ : 1,5290 |
| 64 | 4-methyl-1,2,3-thiadiazole-5-carboxylic acid-(diphenyl-amide) | m.p.: 116°–119° C. |
| 65 | 4-methyl-1,2,3-thiadiazole-5-carboxylic acid-(1-ethinyl-cyclohexylamide) | m.p.: 91°–93° C. |
| 66 | (4-methyl-1,2,3-thiadiazole-5-yl)-pyrrolidinoketone | $n_D^{20}$ : 1,5618 |
| 67 | (4-methyl-1,2,3-thiadiazole-5-yl)-piperidinoketone | $n_D^{20}$ : 1,5550 |
| 68 | 4-methyl-1,2,3-thiadiazole-5-carboxylic acid-(2-furfuryl)-amide | m.p.: 49°–50° C. |
| 69 | (4-methyl-1,2,3-thiadiazole-5-yl)-morpholinoketone | m.p.: 85°–86° C. |
| 70 | 4-methyl-1,2,3-thiadiazole-5-carboxylic acid-(1,-phenyl-ethyl)-amide | m.p.: 78°–79° C. |
| 71 | 4-methyl-1,2,3-thiadiazole-5-carboxylic acid-cyclopropyl-methylamide | $n_D^{20}$ : 1,5470 |
| 72 | 4-methyl-1,2,3-thiadiazole-5-carboxylic acid-morpholino-amide | m.p.: 184°–185° C. |
| 73 | 4-methyl-1,2,3-thiadiazole-5-carboxylic acid-piperidino-amide | m.p.: 155°–156° C. |
| 74 | 4-methyl-1,2,4-thiadiazole-5-carboxylic acid-(N-benzyl-anilide) | m.p.: 83°–84° C. |
| 75 | 4-methyl-1,2,3-thiadiazole-5-carboxylic acid-propylamide | $n_D^{20}$ : 1,5360 |
| 76 | 4-methyl-1,2,3-thiadiazole-5-carboxylic acid-isopropyl-amide | m.p.: 72°–73° C. |
| 77 | 4-methyl-1,2,3-thiadiazole-5-carboxylic acid-cyclohexyl-methylester | $n_D^{20}$ : 1,5176 |
| 78 | 4-methyl-1,2,3-thiadiazole-5-carboxylic acid-(4-chlorobenzyl)-ester | m.p.: 89°–90° C. |
| 79 | 4-methyl-1,2,3-thiadiazole-5-carboxylic acid-benzylester | $n_D^{20}$ : 1,5649 |
| 80 | 4-methyl-1,2,3-thiadiazole-5-carboxylic acid amide | m.p.: 122°–124° C. |
| 81 | 4-methyl-1,2,3-thiadiazole-5-carboxylic acid-(2-methyl-cyclohexylamide) | m.p.: 78°–79°0 C. |
| 82 | 4-methyl-1,2,3-thiadiazole-5-carboxylic acid-(3-methyl-cyclohexylamide) | m.p.: 90°–92° C. |
| 83 | 4-methyl-1,2,3-thiadiazole-5-carboxylic acid-(4-methyl-cyclohexylamide) | m.p.: 118°–120° C. |
| 84 | 4-methyl-1,2,3-thiadiazole-5-carboxylic acid-(tetrahydro-furfurylamide) | $n_D^{20}$ : 1,5471 |
| 85 | 4-methyl-1,2,3-thiadiazole-5-carboxylic acid-(cycloheptyl-methylamide) | $n_D^{20}$ : 1,5476 |
| 86 | 4-methyl-1,2,3-thiadiazole-5-carboxylic acid-(cyclooctyl-methylamide) | $n_D^{20}$ : 1,5439 |
| 87 | 4-propyl-1,2,3-thiadiazole-5-carboxylic acid-(cyclohexyl-methylamide) | m.p.: 51°–52° C. |
| 88 | 4-methyl-1,2,3-thiadiazole-5-carboxylic acid-(1,2,3-tri-methylpropylamide) | m.p.: 95°–96° C. |
| 89 | 4-methyl-1,2,3-thiadiazole-5-carboxylic acid-(3-phenyl-propylamide) | $n_D^{20}$ : 1,5790 |
| 90 | 4-methyl-1,2,3-thiadiazole-5-carboxylic acid-(2-phenyl-ethylamide) | $n_D^{20}$ : 1,5838 |
| 91 | 4-ethyl-1,2,3-thiadiazole-5-carboxylic acid-(cyclohexyl-methylamide) | $n_D^{20}$ : 1,5352 |
| 92 | 4-ethyl-1,2,3-thiadiazole-5-carboxylic acid ethyl ester | b.p.: 74–75/ 0.1 torr |
| 93 | 4-propyl-1,2,3-thiadiazole-5-carboxylic acid | m.p.: 101°–103° C. |
| 94 | 4-methyl-1,2,3-thiadiazole-carboxylic acid-(1,2-diphenyl-ethyl)-amide | m.p.: 158° C. |
| 95 | 4-methyl-1,2,3-thiadiazole 5-carboxylic acid-N-(2-cyanoethyl)-benzyl]amide | m.p.: 81° C. |
| 96 | 4-methyl-1,2,3-thiadiazole-5-carboxylic acid-[1-4-fluoro-phenyl)-ethyl]-amide | m.p.: 112° C. |
| 97 | 4-methyl-1,2,3-thiadiazole-carboxylic acid-(N-methyl-cyclohexylmethyl)-amide | $n_D^{20}$ : 1,5414 |
| 98 | 4-propyl-1,2,3-thiadiazole-5-carboxylic acid-(4-methylbenzyl-amide | m.p.: 78° C. |
| 99 | 4-propyl-1,2,3-thiadiazole-5-carboxylic acid-(4-chlorobenzyl)-amide | m.p.: 102°–103° C. |
| 100 | 4-propyl-1,2,3-thiadiazole-5-carboxylic acid-(4-fluorobenzyl)-amide | m.p.: 77°–78° C. |
| 101 | 4-propyl-1,2,3-thiadiazole-5-carboxylic acid-(3,4-dichloro-benzyl)-amide | m.p.: 97°–98° C. |
| 102 | 4-propyl-1,2,3-thiadiazole-5-carboxylic acid-cyclohexylamide | m.p. 74°–75° C. |
| 103 | 4-propyl-1,2,3-thiadiazole-5-carboxylic acid-(2-methylcyclo-hexylamide) | m.p.: 85° C. |

-continued

| Compound No. | Name of Compound | Physical Constants |
|---|---|---|
| 104 | 4-propyl-1,2,3-thiadiazole-5-carboxylic acid-(3-methylcyclohexylamide) | m.p.: 70° C. |
| 105 | 4-propyl-1,2,3-thiadiazole-5-carboxylic acid-(4-methylcyclohexylamide) | $n_D^{20}$ : 1,5319 |
| 106 | 4-propyl-1,2,3-thiadiazole-5-carboxylic acid-(cycloheptylmethyl)-amide | m.p.: 40°–42° C. |
| 107 | 4-propyl-1,2,3-thiadiazole-carboxylic acid-(cyclooctylmethyl)-amide | $n_D^{20}$ : 1,5323 |
| 108 | 4-methyl-1,2,3-thiadiazole-5-carboxylic acid-(3-hydroxyanilide) | m.p. 176°–177° C. |
| 109 | 4-methyl-1,2,3-thiadiazole-carboxylic acid-(4-chlorophenyl-ester) | m.p.: 71°–74° C. |
| 110 | 1,2,3-thiadiazole-5-carboxylic acid-(cyclohexylmethyl)-amide | m.p.: 115°–116° C. |
| 111 | 4-methyl1,2,3-thiadiazole-5-carboxylic acid-(3,4-dichlorophenylester) | m.p.: 66°–68° C. |
| 112 | 4-methyl-1,2,3-thiadiazole-5-carboxylic acid phenylester | $n_D^{20}$ : 1,5695 |
| 113 | 4-methyl-1,2,3-thiadiazole-5-carboxylic acid-(1,2-dimethylbutyl)-amide | $n_D^{20}$ : 1,5159 |
| 114 | 4-methyl-1,2,3-thiadiazole-5-carboxylic acid-(3-methylbutyl)-amide | $n_D^{20}$ : 1,5243 |
| 115 | 4-methyl-1,2,3-thiadiazole-5-carboxylic acid-(1-hydroxycyclohexylmethyl)-amide | m.p.: 74°–75° C. |
| 116 | 4-methyl-1,2,3-thiadiazole-5-carboxylic acid-(2-dimethylaminoethyl)-amide | $n_D^{20}$ : 1,5360 |
| 117 | 4-methyl-1,2,3-thiadiazole-5-carboxylic acid-(3,3-dimethylbutyl)-amide | m.p. 50°–52° C. |
| 118 | 4-methyl-1,2,3-thiadiazole-5-carboxylic acid-(3-phenoxbenzyl)-ester | $n_D^{20}$ : 1,5989 |
| 119 | 4-methyl-1,2,3-thiadiazole-5-carboxylic acid-(3-methylcarbamoyloxy-anilide) | m.p.: 173° C. (decomposed) |

The compounds of the invention normally are colorless, non-smelling, crystalline materials or liquids which have a poor solubility in water, a moderate solubility in aliphatic hydrocarbons such as petrolether and cyclohexane, and are well soluble in halogenated hydrocarbons such as chloroform and carbontetrachloride; and aromatic hydrocarbons such as benzene, toluene, and xylene; ethers, such as diethylether, tetrahydrofuran and dioxane; carboxylic acid nitriles, such as acetonitrile; ketones, such as acetone; alcohols, such as methanol and ethanol; carboxylic acid amides, such as dimethylformamide and sulfoxides, such as dimethylsulfoxide.

As solvents for the recrystallization there are preferred cyclohexane, acetonitrile and alcohol. The 1,2,3-thiadiazole-5-carboxylic acid and their metal salts have a good water solubility but are only poorly soluble in organic solvents.

The starting products for making the compounds of the invention are conventional.

The following examples will further illustrate the applications and uses of the compounds of the invention.

APPLICATIONS AND USES

EXAMPLE 5

The compounds of the invention appearing from Table I below were emulsified or suspended in an amount of 5 kg of active agent per about 2.5 acres in 600 liter water per about 2.5 acres and were then applied by spraying in a hothouse in a preemergence and postemergence application to the following test plants which in the Table are indicated with the abbreviations listed as follows: Sinapis (Si), Solanum (So), Beta (Be), Gossypium (Go), Hordeum (Ho), Zea mays (Ze), Lolium (Lo) and Setaria (Se).

Three weeks after treatment the results were evaluated on the following scale:

0 = no effect

1–2 = growth regulating effects in the form of an intensive coloring of the primary leaves, retardation, stimulation of the budding or shoots, growth depression and diminution of the leaves, lower root development;

3–4 = plants no longer viable, or withered away.

The letter V in the following Table indicates preemergence application and the letter N indicates postemergence application.

TABLE I

| Compound of the invention | Si V | Si N | So V | So N | Be V | Be N | Go V | Go N | Ho V | Ho N | Ze V | Ze N | Lo V | Lo N | Se V | Se N |
|---|---|---|---|---|---|---|---|---|---|---|---|---|---|---|---|---|
| 4-methyl-1,2,3-thiadiazole-5-carboxylic acid | 0 | 3 | 0 | 4 | 1 | 3 | 0 | 0 | 0 | 3 | 0 | 3 | 1 | 1 | 0 | 3 |
| 4-methyl-1,2,3-thiadiazole-5-carboxylic acid anilide | 0 | 0 | 0 | 0 | 0 | 0 | 0 | 2 | 0 | 0 | 0 | 0 | 0 | 0 | 0 | 0 |
| 4-methyl-1,2,3-thiadiazole-5-carboxylic acid-(2-chloroanilide) | 0 | 3 | 1 | 3 | 0 | 3 | 0 | 0 | 0 | 1 | 0 | 0 | 2 | 3 | 0 | 3 |
| 4-methyl-1,2,3-thiadiazole-5-carboxylic acid-(3-chloroanilide) | 0 | 4 | 0 | 3 | 0 | 4 | 0 | 1 | 0 | 2 | 0 | 0 | 0 | 2 | 0 | 3 |
| 4-methyl-1,2,3-thiadiazole-5-carboxylic acid-(3-methylanilide) | 0 | 4 | 0 | 4 | 0 | 4 | 0 | 0 | 0 | 0 | 0 | 2 | 1 | 1 | 3 | 3 |
| 4-methyl-1,2,3-thiadiazole-5-carboxylic acid-(4-methyl-anilide) | 0 | 0 | 0 | 0 | 0 | 0 | 0 | 2 | 0 | 0 | 0 | 0 | 0 | 0 | 0 | 1 |
| 4-methyl-1,2,3-thiadiazole-5-carboxylic acid-(4-fluoro-anilide) | 0 | 4 | 0 | 2 | 0 | 4 | 0 | 0 | 0 | 0 | 0 | 0 | 1 | 2 | 0 | 3 |
| 4-methyl-1,2,3-thiadiazole-5-carboxylic acid-(3-trifluoromethylanilide) | 0 | 3 | 0 | 0 | 0 | 3 | 0 | 0 | 0 | 0 | 0 | 0 | 1 | 0 | 0 | 3 |
| 4-methyl-1,2,3-thiadiazole-5-carboxylic acid-(N-benzyl-N-2-propinylamide) | 1 | 0 | 0 | 2 | 0 | 3 | 0 | 0 | 0 | 3 | 0 | 0 | 0 | 0 | 0 | 4 |
| 4-methyl-1,2,3-thiadiazole-5-carboxylic acid-(4-chloroanilide) | 0 | 0 | 0 | 0 | 0 | 1 | 0 | 0 | 0 | 1 | 0 | 1 | 0 | 0 | 0 | 1 |

TABLE I-continued

| Compound of the invention | Si V | Si N | So V | So N | Be V | Be N | Go V | Go N | Ho V | Ho N | Ze V | Ze N | Lo V | Lo N | Se V | Se N |
|---|---|---|---|---|---|---|---|---|---|---|---|---|---|---|---|---|
| 4-methyl-1,2,3-thiadiazole-5-carboxylic acid-(3,5-dichloro-anilide) | | | | | | | | | | | | | | | | |
| 4-methyl-1,2,3-thiadiazole-5-carboxylic acid benzylamide | 1 | 4 | 2 | 3 | 3 | 3 | 1 | 3 | 3 | 3 | 1 | 3 | 3 | 3 | 3 | 4 |
| 4-methyl-1,2,3-thiadiazole-5-carboxylic acid-(4-chloro-benzylamide) | 4 | 4 | 4 | 3 | 4 | 4 | 2 | 3 | 4 | 3 | 2 | 2 | 4 | 3 | 4 | 4 |
| 4-methyl-1,2,3-thiadiazole-5-carboxylic acid-(2-chloro-6-methylanilide) | 3 | 2 | 3 | 2 | 0 | 0 | 0 | 0 | 0 | 0 | 0 | 0 | 0 | 0 | 2 | 3 |
| 4-methyl-1,2,3-thiadiazole-5-carboxylic acid-(2,6-dichloro-anilide) | 1 | 4 | 2 | 3 | 0 | 2 | 0 | 1 | 1 | 1 | 0 | 0 | 0 | 1 | 2 | 2 |
| 4-methyl-1,2,3-thiadiazole-5-carboxylic acid diethylamide | 0 | 0 | 0 | 1 | 0 | 0 | 0 | 1 | 0 | 0 | 0 | 0 | 0 | 0 | 0 | 0 |
| 4-methyl-1,2,3-thiadiazole-5-carboxylic acid-(2-pyridyl-methylamide) | 0 | 1 | 0 | 1 | 1 | 0 | 0 | 1 | 0 | 0 | 0 | 0 | 0 | 0 | 0 | 0 |
| 4-methyl-1,2,3-thiadiazole-5-carboxylic acid-(2-chloro-benzyl-amide) | 2 | 2 | 3 | 2 | 2 | 1 | 0 | 1 | 2 | 0 | 0 | 0 | 4 | 1 | 3 | 1 |
| 4-methyl-1,2,3-thiadiazole-5-carboxylic acid-(cyclohexyl-methyl)-amide | 4 | 4 | 4 | 4 | 4 | 4 | 4 | 4 | 4 | 2 | 4 | 2 | 4 | 4 | 4 | 4 |
| 4-methyl-1,2,3-thiadiazole-5-carboxylic acid-(3,4-methylene-dioxybenzylamide) | 2 | 2 | 1 | 0 | 0 | 0 | 0 | 1 | 1 | 1 | 0 | 0 | 1 | 1 | 1 | 1 |
| 4-methyl-1,2,3-thiadiazole-5-carboxylic acid-(2,4-dichloro-benzylamide) | 0 | 3 | 0 | 0 | 0 | 2 | 0 | 0 | 0 | 0 | 0 | 0 | 1 | 1 | 0 | 4 |
| 4-methyl-1,2,3-thiadiazole-5-carboxylic acid-(3,4-dichloro-benzylamide) | 0 | 1 | 0 | 0 | 0 | 1 | 0 | 1 | 0 | 0 | 0 | 1 | 0 | 0 | 0 | 1 |
| 4-methyl-1,2,3-thiadiazole-5-carboxylic acid-(3-chloro-benzylamide) | 0 | 1 | 0 | 0 | 0 | 1 | 0 | 1 | 0 | 1 | 0 | 1 | 0 | 0 | 0 | 1 |
| 4-methyl-1,2,3-thiadiazole-5-carboxylic acid-(2-methoxy-benzylamide) | 0 | 0 | 0 | 0 | 1 | 0 | 0 | 0 | 0 | 0 | 0 | 0 | 0 | 0 | 0 | 0 |
| 4-methyl-1,2,3-thiadiazole-5-carboxylic acid-(4-fluoro-benzylamide) | 4 | 4 | 4 | 4 | 4 | 4 | 3 | 4 | 4 | 2 | 3 | 1 | 4 | 4 | 4 | 4 |
| 4-methyl-1,2,3-thiadiazole-5-carboxylic acid-(4-methyl-benzylamide) | 3 | 1 | 3 | 3 | 1 | 0 | 1 | 2 | 2 | 0 | 0 | 0 | 3 | 1 | 3 | 2 |
| 4-methyl-1,2,3-thiadiazole-5-carboxylic acid-(2-fluoro-benzylamide) | 4 | 4 | 4 | 4 | 4 | 4 | 4 | 4 | 4 | 4 | 2 | 0 | 4 | 4 | 4 | 4 |
| 4-methyl-1,2,3-thiadiazole-5-carboxylic acid-cyclohexylamide | 4 | 4 | 4 | 3 | 4 | 4 | 3 | 3 | 3 | 3 | 3 | 2 | 4 | 4 | 4 | 4 |
| 4-methyl-1,2,3-thiadiazole-5-carboxylic acid-cyclohexylamide | 2 | 4 | 4 | 3 | 2 | 4 | 2 | 3 | 3 | 2 | 2 | 2 | 3 | 2 | 1 | 3 |
| 4-methyl-1,2,3-thiadiazole-5-carboxylic acid-cycloheptylamide | 4 | 4 | 4 | 3 | 4 | 4 | 2 | 3 | 3 | 2 | 2 | 0 | 3 | 2 | 2 | 1 |
| 4-methyl-1,2,3-thiadiazole-5-carboxylic acid-cyclopentylamide | 1 | 2 | 1 | 0 | 0 | 1 | 0 | 0 | 0 | 0 | 0 | 0 | 1 | 0 | 0 | 0 |
| 4-methyl-1,2,3-thiadiazole-5-carboxylic acid-cyclopropylamide | 1 | 1 | 1 | 0 | 0 | 1 | 0 | 0 | 0 | 1 | 0 | 0 | 0 | 0 | 0 | 0 |
| 4-methyl-1,2,3-thiadiazole-5-carboxylic acid butylamide | 3 | 3 | 2 | 1 | 4 | 3 | 2 | 3 | 1 | 1 | 0 | 0 | 1 | 1 | 3 | 2 |
| 4-methyl-1,2,3-thiadiazole-5-carboxylic acid-(2-furfuryl)-amide | 0 | 0 | 0 | 0 | 0 | 1 | 0 | 0 | 0 | 1 | 0 | 0 | 0 | 0 | 0 | 1 |
| 4-methyl-1,2,3-thiadiazole-5-carboxylic acid-(1-phenylethyl)-amide | 0 | 0 | 0 | 0 | 0 | 1 | 0 | 0 | 0 | 0 | 0 | 0 | 0 | 0 | 0 | 0 |
| 4-methyl-1,2,3-thiadiazole-5-carboxylic acid-cyclopropylmethylamide | 0 | 1 | 0 | 0 | 0 | 3 | 0 | 1 | 0 | 0 | 0 | 0 | 0 | 0 | 0 | 0 |
| 4-methyl-1,2,3-thiadiazole-5-carboxylic acid-morpholino-amide | 0 | 0 | 1 | 0 | 0 | 0 | 0 | 0 | 0 | 0 | 0 | 0 | 0 | 0 | 0 | 0 |
| 4-methyl-1,2,3-thiadiazole-5-carboxylic acid-piperidino-1mide | 0 | 0 | 0 | 0 | 0 | 0 | 0 | 0 | 0 | 3 | 0 | 0 | 0 | 0 | 0 | 0 |
| 4-methyl-1,2,3-thiadiazole-5-carboxylic acid-(N-benzylanilide) | 0 | 0 | 0 | 0 | 0 | 1 | 0 | 0 | 0 | 3 | 0 | 0 | 0 | 0 | 0 | 0 |
| 4-methyl-1,2,3-thiadiazole-5-carboxylic acid-propylamide | 0 | 0 | 0 | 0 | 0 | 0 | 0 | 0 | 0 | 3 | 0 | 0 | 0 | 0 | 0 | 0 |
| 4-methyl-1,2,3-thiadiazole-5-carboxylic acid-isopropylamide | 0 | 0 | 0 | 0 | 0 | 0 | 0 | 1 | 0 | 1 | 0 | 0 | 0 | 0 | 0 | 0 |
| 4-methyl-1,2,3-thiadiazole-5-carboxylic acid-cyclohexylmethylester | 0 | 0 | 0 | 3 | 0 | 1 | 0 | 1 | 0 | 1 | 0 | 0 | 0 | 1 | 0 | 0 |
| 4-methyl-1,2,3-thiadiazole-5-yl)- | | | | | | | | | | | | | | | | |

TABLE I-continued

| Compound of the invention | Si V | Si N | So V | So N | Be V | Be N | Go V | Go N | Ho V | Ho N | Ze V | Ze N | Lo V | Lo N | Se V | Se N |
|---|---|---|---|---|---|---|---|---|---|---|---|---|---|---|---|---|
| morpholinoketone | 0 | 0 | 0 | 0 | 0 | 1 | 0 | 0 | 0 | 1 | 0 | 1 | 0 | 0 | 0 | 1 |
| 4-methyl-1,2,3-thiadiazole-5-carboxylic acid-(4-chlorobenzyl)-ester | 0 | 2 | 0 | 3 | 0 | 3 | 0 | 2 | 0 | 1 | 0 | 0 | 0 | 1 | 0 | 1 |
| 4-methyl-1,2,3-thiadiazole-5-carboxylic acid-benzylester | 0 | 1 | 0 | 3 | 0 | 2 | 0 | 2 | 0 | 2 | 0 | 0 | 0 | 1 | 0 | 1 |
| 4-methyl-1,2,3-thiadiazole-5-carboxylic acid amide | 0 | 1 | 0 | 1 | 0 | 0 | 0 | 0 | 0 | 0 | 0 | 0 | 0 | 0 | 0 | 0 |
| 4-methyl-1,2,3-thiadiazole-5-carboxylic acid-(2-methylcyclohexylamide) | 4 | 4 | 4 | 4 | 4 | 4 | 0 | 0 | 4 | 2 | 2 | 0 | 4 | 4 | 4 | 4 |
| 4-methyl-1,2,3-thiadiazole-5-carboxylic acid-(3-methylcyclohexylamide) | 4 | 4 | 4 | 4 | 4 | 4 | 0 | 0 | 4 | 4 | 4 | 4 | 4 | 4 | 4 | 4 |
| 4-methyl-1,2,3-thiadiazole-5-carboxylic acid-(4-methylcyclohexylamide) | 2 | 2 | 4 | 2 | 2 | 0 | 0 | 0 | 2 | 0 | 0 | 0 | 2 | 2 | 2 | 4 |
| 4-methyl-1,2,3-thiadiazole-5-carboxylic acid-(tetrahydrofurfurylamide) | 4 | 4 | 2 | 2 | 3 | 2 | 0 | 0 | 0 | 0 | 0 | 0 | 3 | 2 | 2 | 1 |
| 4-methyl-1,2,3-thiadiazole-5-carboxylic acid-(cycloheptylmethylamide) | 4 | 4 | 4 | 4 | 4 | 4 | 0 | 0 | 4 | 4 | 4 | 4 | 4 | 4 | 4 | 4 |
| 4-methyl-1,2,3-thiadiazole-5-carboxylic acid-(cyclooctylmethylamide) | 4 | 4 | 4 | 4 | 4 | 4 | 0 | 0 | 4 | 4 | 4 | 4 | 4 | 4 | 4 | 4 |
| 4-propyl-1,2,3-thiadiazole-5-carboxylic acid-(cyclohexylmethylamide) | 0 | 2 | 0 | 0 | 0 | 0 | 0 | 0 | 0 | 0 | 0 | 0 | 0 | 0 | 0 | 0 |
| 4-methyl-1,2,3-thiadiazole-5-carboxylic acid-(1,2,2-trimethylpropyl-amide) | 0 | 2 | 0 | 2 | 0 | 0 | 0 | 0 | 0 | 0 | 0 | 0 | 0 | 0 | 0 | 0 |
| 4-methyl-1,2,3-thiadiazole-5-carboxylic acid-(2-phenylethylamide) | 0 | 2 | 0 | 2 | 0 | 2 | 0 | 0 | 0 | 0 | 0 | 0 | 0 | 2 | 0 | 0 |
| 4-ethyl-1,2,3-thiadiazole-5-carboxylic acid-(cyclohexylmethylamide) | 3 | 4 | 4 | 3 | 4 | 4 | 0 | 2 | 0 | 0 | 0 | 0 | 0 | 2 | 0 | 2 |
| 4-ethyl-1,2,3-thiadiazole-5-carboxylic acid ethylester | 0 | 0 | 0 | 0 | 1 | 1 | 0 | 0 | 0 | 0 | 0 | 0 | 0 | 0 | 0 | 0 |
| 4-propyl-1,2,3-thiadiazole-5-carboxylic acid | 0 | 0 | 3 | 3 | 0 | 0 | 0 | 0 | 0 | 0 | 0 | 0 | 0 | 0 | 0 | 0 |
| 4-propyl-1,2,3-thiadiazole-5-carboxylic acid-(4-methyl-benzyl)-amide | 1 | 1 | 0 | 0 | 0 | 0 | 0 | 0 | 0 | 0 | 0 | 0 | 0 | 0 | 0 | 0 |
| 4-propyl-1,2,3-thiadiazole-5-carboxylic acid-(4-chloro-benzyl)-amide | 1 | 1 | 0 | 0 | 0 | 0 | 0 | 0 | 0 | 0 | 0 | 0 | 0 | 0 | 0 | 0 |
| 4-propyl-1,2,3-thiadiazole-5-carboxylic acid-(4-fluoro-benzyl)-amide | 1 | 1 | 0 | 0 | 0 | 0 | 0 | 0 | 0 | 0 | 0 | 0 | 0 | 0 | 0 | 0 |
| 4-propyl-1,2,3-thiadiazole-5-carboxylic acid-(3,4-dichloro-benzyl)-amide | 1 | 1 | 0 | 0 | 0 | 0 | 0 | 0 | 0 | 0 | 0 | 0 | 0 | 0 | 0 | 0 |
| 4-propyl-1,2,3-thiadiazole-5-carboxylic acid-cyclohexylamide | 1 | 1 | 0 | 0 | 0 | 0 | 0 | 0 | 0 | 0 | 0 | 0 | 0 | 0 | 0 | 0 |
| 4-propyl-1,2,3-thiadiazole-5-carboxylic acid-(2-methylcyclohexylamide) | 1 | 1 | 0 | 0 | 0 | 0 | 0 | 0 | 0 | 0 | 0 | 0 | 0 | 0 | 0 | 0 |
| 4-propyl-1,2,3-thiadiazole-5-carboxylic acid-(3-methylcyclohexylamide) | 1 | 1 | 0 | 0 | 0 | 0 | 0 | 0 | 0 | 0 | 0 | 0 | 0 | 0 | 0 | 0 |
| 4-propyl-1,2,3-thiadiazole-5-carboxylic acid-(4-methylcyclohexylamide) | 1 | 1 | 0 | 0 | 1 | 1 | 0 | 0 | 0 | 0 | 0 | 0 | 0 | 0 | 0 | 0 |
| 4-propyl-1,2,3-thiadiazole-5-carboxylic acid-(cyclooctyl-methyl)-amide | 3 | 3 | 0 | 0 | 0 | 0 | 0 | 0 | 0 | 0 | 0 | 0 | 0 | 0 | 0 | 0 |
| 4-propyl-1,2,3-thiadiazole-5-carboxylic acid-(cycloheptyl-methyl)-amide | 3 | 3 | 1 | 1 | 0 | 0 | 0 | 0 | 0 | 0 | 0 | 0 | 0 | 0 | 0 | 0 |
| 4-methyl-1,2,3-thiadiazole-5-carboxylic acid-(1,2-diphenyl-ethyl)-amide | 0 | 0 | 0 | 0 | 0 | 0 | 0 | 0 | 0 | 0 | 0 | 0 | 0 | 0 | 2 | 2 |
| 4-methyl-1,2,3-thiadiazole-5-carboxylic acid-[N-(2-cyanoethyl)-benzyl]-amide | 1 | 1 | 0 | 0 | 0 | 0 | 0 | 0 | 0 | 0 | 0 | 0 | 0 | 0 | 0 | 0 |
| 4-methyl-1,2,3-thiadiazole-5-carboxylic acid-[1-(4-fluoro-phenyl)-ethyl]-amide | 4 | 4 | 0 | 0 | 0 | 0 | 0 | 0 | 1 | 1 | 0 | 0 | 0 | 0 | 4 | 4 |
| 4-methyl-1,2,3-thiadiazole-5-carboxylic acid-(N-methyl-cyclohexylmethyl)-amide | 4 | 4 | 4 | 4 | 4 | 4 | 0 | 2 | 0 | 0 | 0 | 0 | 0 | 0 | 0 | 2 |
| 4-methyl-1,2,3-thiadiazole-5-carboxylic acid-(3-hydroxyanilide) | 1 | 1 | 0 | 0 | 0 | 0 | 0 | 0 | 0 | 0 | 0 | 0 | 0 | 0 | 0 | 0 |
| 4-methyl-1,2,3-thiadiazole-5-carboxylic acid-(1-hydroxy-cyclo- | 4 | 4 | 4 | 4 | 4 | 4 | 4 | 4 | 4 | 3 | 4 | 3 | 4 | 3 | 4 | 3 |

TABLE I-continued

| Compound of the invention | Si V | Si N | So V | So N | Be V | Be N | Go V | Go N | Ho V | Ho N | Ze V | Ze N | Lo V | Lo N | Se V | Se N |
|---|---|---|---|---|---|---|---|---|---|---|---|---|---|---|---|---|
| hexylmethyl)-amide |  |  |  |  |  |  |  |  |  |  |  |  |  |  |  |  |
| 4-methyl-1,2,3-thiadiazole-5-carboxylic acid phenylester | — | 2 | — | 2 | — | 1 | — | 1 | — | 1 | — | 1 | — | 1 | — | 2 |
| 4-methyl-1,2,3-thiadiazole-5-carboxylic acid-(1,3-dimethylbutyl)-amide | — | 3 | — | 2 | — | 2 | — | 3 | — | 3 | — | 0 | — | 0 | — | 3 |
| 4-methyl-1,2,3-thiadiazole-5-carboxylic acid-(3-methylbutyl)-amide | 4 | 4 | 4 | 4 | 4 | 4 | 4 | 4 | 3 | 2 | 3 | 2 | 4 | 1 | 4 | 4 |
| 4-methyl-1,2,3-thiadiazole-5-carboxylic acid-(2-dimethylaminoethyl)-amide | — | — | — | — | — | — | — | — | — | — | — | — | — | — | — | — |
| 4-methyl-1,2,3-thiadiazole-5-carboxylic acid-(3-phenoxybenzyl)-ester | 1 | — | 1 | — | — | — | — | — | — | — | — | — | — | — | — | — |
| 4-methyl-1,2,3-thiadiazole-5-carboxylic acid-(3-methylcarbamoyloxy-anilide) | — | — | — | — | — | — | — | — | — | — | — | — | — | — | — | — |
| 4-methyl-1,2,3-thiadiazole-5-carboxylic acid-(3,3-dimethylbutyl)-amide | 4 | 4 | 4 | 4 | 4 | 4 | 3 | 3 | 2 | 1 | 1 | 4 | 1 | 4 | 4 | 2 |

Analogous activity have the following compounds:
4-methyl-1,2,3-thiadiazole-5-carboxylic acid-(N-ethyl-N-benzylamide).
4-methyl-1,2,3-thiadiazole-5-carboxylic acid-(N-benzyl-N-isopropylamide).
4-methyl-1,2,3-thiadiazole-5-carboxylic acid-(N-benzyl-N-butylamide).
4-methyl-1,2,3-thiadiazole-5-carboxylic acid-(3-methylbenzylamide).
4-methyl-1,2,3-thiadiazole-5-carboxylic acid-(2-naphthylmethyl)-amide.
4-methyl-1,2,3-thiadiazole-5-carboxylic acid-(3,5-dimethylbenzyl)-amide.
4-methyl-1,2,3-thiadiazole-5-carboxylic acid-(4-tert-butylbenzyl)-amide.

EXAMPLE 6

The plants listed below in Table II were treated in a postemergence application with the agents indicated in an amount of 1 kg of active agent per about 2.5 acres. The treatment was effected in a hothouse. The agent for this purpose was applied in a uniform manner to the soil as a suspension in 500 liter water per 2.5 acres.

The results show that the compounds of the invention destroyed a large selection of plant species while the important cultures of maize and cotton were not damaged.

The evaluation was on a scale from 0=total destruction to 10=no injury to plant.

TABLE II

| Compounds of the invention | maize | cotton | Stellaria | Senecio | Matricaria | Lamium | Centaurea | Amaranthus | Galium | Chrysanthemum | Ipomoea | Polygonum |
|---|---|---|---|---|---|---|---|---|---|---|---|---|
| 4-methyl-1,2,3-thiadiazole-5-carboxylic acid-(cyclohexylmethyl)-amide | 10 | 10 | 0 | 0 | 0 | 0 | 0 | 0 | 0 | 0 | 0 | 0 |
| 4-methyl-1,2,3-thiadiazole-5-carboxylic acid-(4-fluorobenzyl-amide) | 10 | 10 | 0 | 0 | 0 | 0 | 0 | 0 | 0 | 0 | 0 | 0 |
| Untreated | 10 | 10 | 10 | 10 | 10 | 10 | 10 | 10 | 10 | 10 | 10 | 10 |

| Compounds of the invention | Avena | Alopecurus | Echinochloa | Setaria | Digitaria | Cyperus | Sorghum | Poa | Solanum | Datura | Escholtzia | Kochia |
|---|---|---|---|---|---|---|---|---|---|---|---|---|
| 4-methyl-1,2,3-thiadiazole-5-carboxylic acid-(cyclohexylmethyl)-amide | 0 | 0 | 0 | 0 | 0 | 0 | 0 | 0 | 0 | 0 | 0 | 0 |
| 4-methyl-1,2,3-thiadiazole-5-carboxylic acid-(4-fluorobenzyl-amide) | 0 | 0 | 0 | 0 | 0 | 7 | 0 | 0 | 0 | 0 | 0 | 0 |
| Untreated | 10 | 10 | 10 | 10 | 10 | 10 | 10 | 10 | 10 | 10 | 10 | 10 |

EXAMPLE 7

4-methyl-1,2,3-thiadiazole-5-carboxylic acid-(cyclohexylmethyl)-amide and 4-methyl-1,2,3-thiadiazole-5-carboxylic acid-(4-fluorobenzylamide)emulsified in 500 liters of water per 2.5 acres were applied in a hothouse in amounts of 1 kg of active agent per 2.5 acres to the following plants: Stellaria, Senecio, Matricaria, Lamium, Centaurea, Amaranthus, Galium, Chrysanthemum, Ipomoea, Polygonum, Brassica, Solanum, Allium, Pisum, Portulaca, Kochia, Daucus, Cheiranthus, Euphorbia, Datura and Cichorium.

All plants listed were destroyed. Two days later cultures of maize, cotton and soybean were seeded into the treated soil. The cultures remained without damage and could grow free of competitive weeds.

EXAMPLE 8

4-methyl-1,2,3-thiadiazole-5-carboxylic acid-(cyclohexylmethyl)-amide in an amount of 1 kg per 2.5 acres was sprayed in a hothouse in the form of an emulsion with 500 liter of water per 2.5 acres onto the plants listed below in Table 3.

The results show that the agricultural plants rice and maize remained without damage while important weed type grasses were destroyed.

The evaluation was on a scale wherein 0=total destruction and 10=no damage to the plants.

TABLE III

| Compound of the invention | grain | wheat | maize | rice | Echinochloa | Setaria | Digitaria | Alopecurus |
|---|---|---|---|---|---|---|---|---|
| 4-methyl-1,2,3-thiadiazole-5-carboxylic acid-(cyclohexylmethyl)-amide | 10 | 10 | 10 | 10 | 0 | 0 | 0 | 0 |
| 4-methyl-1,2,3-thiadiazole-5-carboxylic acid-(4-fluorobenzylamide) | 10 | 10 | 10 | 10 | 0 | 0 | 0 | 2 |
| untreated | 10 | 10 | 10 | 10 | 10 | 10 | 10 | 10 |

EXAMPLE 9

Potted cotton plants in the stage of the incipient blossom buds were treated with the agent listed in Table 4 and at the dosage also indicated. The treatment was four times repeated. The amount of water to prepare the composition applied was 500 liters per about 2.5 acres.

After a few days the percentage of dropped leaves was determined as proof of the defoliation. The following table shows the superiority of the compound of the invention.

TABLE IV

| Compound of the invention | active agent kg/about 2.5 acres | defoliation |
|---|---|---|
| 4-methyl-1,2,3-thiadiazole-5-carboxylic acid-(cyclohexylmethyl)-amide | 0.05 | 68.8 |
| comparison compound (U.S. Pat. No. 2,954,407) tri-n-butyl-trithiophosphate | 0.05 | 10.0 |
| | 0.50 | 53.3 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compound of the formula

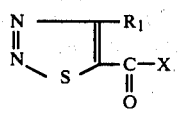

wherein
$R_1$ is hydrogen, $C_1$-$C_4$ alkyl, chloromethyl, or bromomethyl; and
X has the formula

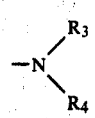

where $R_3$ and $R_4$ are the same or different and are hydrogen, $C_1$-$C_{18}$ alkyl, mono- or disubstituted $C_1$-$C_{18}$ alkyl substituted in the 1-, 2- or 3-position by halogen, $C_1$-$C_6$ alkoxy, phenoxy, dimethylamino, diethylamino, methoxycarbonyl, ethoxycarbonyl or cyano, tetrahydrofurfuryl, $C_3$-$C_8$ cycloalkylmethyl, $C_2$-$C_8$ 2- or 3-alkenyl or alkinyl, phenyl or diphenyl $C_1$-$C_3$ alkyl, mono- or disubstituted benzyl substituted by one or more of halogen, methylenedioxy, $C_1$-$C_6$ alkyl, $C_1$-$C_6$ alkoxy, trifluoromethyl or nitro, α-methyl- or α,α-dimethylbenzyl, pyridyl, furfuryl, $C_3$-$C_8$ cycloalkyl, $C_1$-$C_6$ alkyl or ethinyl substituted $C_3$-$C_8$ cycloalkyl, phenyl, mono- or disubstituted phenyl substituted by one or more of halogen, methylenedioxy, $C_1$-$C_6$ alkyl, $C_1$-$C_6$ alkoxy, trifluoromethyl or nitro, or naphthyl, or $R_3$ and $R_4$ together with the adjoining nitrogen atom constitute a morpholine, piperidine or pyrrolidine group.

2. A herbicidal and growth regulating composition for plants comprising about 10 to 80% by weight of the active agent defined in claim 1 and about 90 to 20% by weight of liquid or solid carrier materials in which composition part of the carrier materials may be replaced by up to 20% by weight of surface active agents.

3. The compound of claim 1 which is 4-methyl-1,2,3-thiadiazole-5-carboxylic acid-(4-fluorobenzylamide).

4. The compound of claim 1 which is 4-methyl-1,2,3-thiadiazole-5-carboxylic acid-(cyclohexylmethyl)-amide.

5. The compound of claim 1 which is 4-methyl-1,2,3-thiadiazole-5-carboxylic acid-anilide.

6. The compound of claim 1 which is 4-methyl-1,2,3-thiadiazole-5-carboxylic acid-(2-chloro-anilide).

7. The compound of claim 1 which is 4-methyl-1,2,3-thiadiazole-5-carboxylic acid-(3-chloroanilide).

8. The compound of claim 1 which is 4-methyl-1,2,3-thiadiazole-5-carboxylic acid-(3,4-dichloroanilide).

9. The compound of claim 1 which is 4-methyl-1,2,3-thiadiazole-5-carboxylic acid-(4-chloro-2-methylanilide).

10. The compound of claim 1 which is 4-methyl-1,2,3-thiadiazole-5-carboxylic acid-(2-methylanilide).

11. The compound of claim 1 which is 4-methyl-1,2,3-thiadiazole-5-carboxylic acid-(3-methylanilide).

12. The compound of claim 1 which is 4-methyl-1,2,3-thiadiazole-5-carboxylic acid-(4-methylanilide).

13. The compound of claim 1 which is 4-methyl-1,2,3-thiadiazole-5-carboxylic acid-(4-fluoroanilide).

14. The compound of claim 1 which is 4-methyl-1,2,3-thiadiazole-5-carboxylic acid-(3-trifluoromethylanilide).

15. The compound of claim 1 which is 4-methyl-1,2,3-thiadiazole-5-carboxylic acid-(4-nitroanilide).

16. The compound of claim 1 which is 4-methyl-1,2,3-thiadiazole-5-carboxylic acid-(N-methylanilide).

17. The compound of claim 1 which is 4-methyl-1,2,3-thiadiazole-5-carboxylic acid-dimethylamide.

18. The compound of claim 1 which is 4-methyl-1,2,3-thiadiazole-5-carboxylic acid-(N-benzyl-N-2-propinylamide).

19. The compound of claim 1 which is 4-methyl-1,2,3-thiadiazole-5-carboxylic acid-(4-chloroanilide).

20. The compound of claim 1 which is 4-methyl-1,2,3-thiadiazole-5-carboxylic acid-(3,5-dichloroanilide).

21. The compound of claim 1 which is 4-methyl-1,2,3-thiadiazole-5-carboxylic acid-benzylamide.

22. The compound of claim 1 which is 4-methyl-1,2,3-thiadiazole-5-carboxylic acid-(4-chlorobenzylamide).

23. The compound of claim 1 which is 4-methyl-1,2,3-thiadiazole-5-carboxylic acid-(2-chloro-6-methylanilide).

24. The compound of claim 1 which is 4-methyl-1,2,3-thiadiazole-5-carboxylic acid-(N-cyanmethyl-2,6-dimethylanilide).

25. The compound of claim 1 which is 4-methyl-1,2,3-thiadiazole-5-carboxylic acid-(2,6-dimethylanilide).

26. The compound of claim 1 which is 4-methyl-1,2,3-thiadiazole-5-carboxylic acid-(2,6-dichloroanilide).

27. The compound of claim 1 which is 4-methyl-1,2,3-thiadiazole-5-carboxylic acid-diethylamide.

28. The compound of claim 1 which is 4-methyl-1,2,3-thiadiazole-5-carboxylic acid-(2-pyridylmethylamide).

29. The compound of claim 1 which is 4-methyl-1,2,3-thiadiazole-5-carboxylic acid-(3-pyridylmethylamide).

30. The compound of claim 1 which is 4-methyl-1,2,3-thiadiazole-5-carboxylic acid-(2-chlorobenzylamide).

31. The compound of claim 1 which is 4-methyl-1,2,3-thiadiazole-5-carboxylic acid-(3,4-methylendioxybenzylamide).

32. The compound of claim 1 which is 4-methyl-1,2,3-thiadiazole-5-carboxylic acid-diisopropylamide.

33. The compound of claim 1 which is 4-methyl-1,2,3-thiadiazole-5-carboxylic acid-(N-benzyl-N-methylamide).

34. The compound of claim 1 which is 4-methyl-1,2,3-thiadiazole-5-carboxylic acid-(2,4-dichlorobenzylamide).

35. The compound of claim 1 which is 4-methyl-1,2,3-thiadiazole-5-carboxylic acid-(3,4-dichlorobenzylamide).

36. The compound of claim 1 which is 4-methyl-1,2,3-thiadiazole-5-carboxylic acid-(3-chlorobenzylamide).

37. The compound of claim 1 which is 4-methyl-1,2,3-thiadiazole-5-carboxylic acid-(2-methoxybenzylamide).

38. The compound of claim 1 which is 4-methyl-1,2,3-thiadiazole-5-carboxylic acid-(3-methoxybenzylamide).

39. The compound of claim 1 which is 4-methyl-1,2,3-thiadiazole-5-carboxylic acid-(4-methoxybenzylamide).

40. The compound of claim 1 which is 4-methyl-1,2,3-thiadiazole-5-carboxylic acid-(4-methylbenzylamide).

41. The compound of claim 1 which is 4-methyl-1,2,3-thiadiazole-5-carboxylic acid-(2-fluorobenzylamide).

42. The compound of claim 1 which is 4-methyl-1,2,3-thiadiazole-5-carboxylic acid-(N-ethyl-N-benzylamide).

43. The compound of claim 1 which is 4-methyl-1,2,3-thiadiazole-5-carboxylic acid-(N-benzyl-N-isopropylamide).

44. The compound of claim 1 which is 4-methyl-1,2,3-thiadiazole-5-carboxylic acid-(N-benzyl-N-butylamide).

45. The compound of claim 1 which is 4-methyl-1,2,3-thiadiazole-5-carboxylic acid-(3-methylbenzylamide).

46. The compound of claim 1 which is 4-methyl-1,2,3-thiadiazole-5-carboxylic acid-(2-naphthylmethylamide).

47. The compound of claim 1 which is 4-methyl-1,2,3-thiadiazole-5-carboxylic acid-(3,5-dimethylbenzylamide).

48. The compound of claim 1 which is 4-methyl-1,2,3-thiadiazole-5-carboxylic acid-(4-tert-butylbenzylamide).

49. The compound of claim 1 which is 4-methyl-1,2,3-thiadiazole-5-carboxylic acid-cyclohexylamide.

50. The compound of claim 1 which is 4-methyl-1,2,3-thiadiazole-5-carboxylic acid-cyclooctylamide.

51. The compound of claim 1 which is 4-methyl-1,2,3-thiadiazole-5-carboxylic acid-cycloheptylamide.

52. The compound of claim 1 which is 4-methyl-1,2,3-thiadiazole-5-carboxylic acid-cyclopentylamide.

53. The compound of claim 1 which is 4-methyl-1,2,3-thiadiazole-5-carboxylic acid-cyclopropylamide.

54. The compound of claim 1 which is 4-methyl-1,2,3-thiadiazole-5-carboxylic acid-butylamide.

55. The compound of claim 1 which is 4-methyl-1,2,3-thiadiazole-5-carboxylic acid-(2-methylpropylamide).

56. The compound of claim 1 which is 4-methyl-1,2,3-thiadiazole-5-carboxylic acid-(1,1-dimethylethylamide).

57. The compound of claim 1 which is 4-methyl-1,2,3-thiadiazole-5-carboxylic acid-(2-propenylamide).

58. The compound of claim 1 which is 4-methyl-1,2,3-thiadiazole-5-carboxylic acid-(ethoxycarbonylmethylamide).

59. The compound of claim 1 which is 4-methyl-1,2,3-thiadiazole-5-carboxylic acid-(2-ethoxyethylamide).

60. The compound of claim 1 which is 4-methyl-1,2,3-thiadiazole-5-carboxylic acid-(1,1-diethyl-2-propinylamide).

61. The compound of claim 1 which is 4-methyl-1,2,3-thiadiazole-5-carboxylic acid-(2,2-diethoxyethylamide).

62. The compound of claim 1 which is 4-methyl-1,2,3-thiadiazole-5-carboxylic acid-(3-dimethylaminopropylamide).

63. The compound of claim 1 which is 4-methyl-1,2,3-thiadiazole-5-carboxylic acid-(diphenylamide).

64. The compound of claim 1 which is 4-methyl-1,2,3-thiadiazole-5-carboxylic acid-(1-ethinylcyclohexylamide).

65. The compound of claim 1 which is (4-methyl-1,2,3-thiadiazole-5-yl)-pyrrolidinoketone.

66. The compound of claim 1 which is (4-methyl-1,2,3-thiadiazole-5-yl)-piperidinoketone.

\* \* \* \* \*